United States Patent
Bae et al.

(10) Patent No.: US 12,306,141 B2
(45) Date of Patent: May 20, 2025

(54) WELDING DEFECT INSPECTION METHOD

(71) Applicant: LG ENERGY SOLUTION, LTD., Seoul (KR)

(72) Inventors: Sang Ho Bae, Daejeon (KR); Hun Bum Jung, Daejeon (KR); Ji Hun Hwang, Daejeon (KR); Cha Hun Ku, Daejeon (KR); Su Taek Jung, Daejeon (KR); Chang Min Han, Daejeon (KR); Joo Young Chung, Daejeon (KR); Yong Jun Lee, Daejeon (KR); Jae Hwa Choi, Daejeon (KR); Young Seok Baek, Daejeon (KR); Jin Yong Lee, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 289 days.

(21) Appl. No.: 17/908,719

(22) PCT Filed: Jun. 16, 2021

(86) PCT No.: PCT/KR2021/007545
§ 371 (c)(1),
(2) Date: Sep. 1, 2022

(87) PCT Pub. No.: WO2022/039360
PCT Pub. Date: Feb. 24, 2022

(65) Prior Publication Data
US 2023/0134729 A1  May 4, 2023

(30) Foreign Application Priority Data
Aug. 21, 2020 (KR) .................... 10-2020-0105340

(51) Int. Cl.
*G01N 3/02* (2006.01)
*G01N 33/2045* (2019.01)
(Continued)

(52) U.S. Cl.
CPC .......... *G01N 3/02* (2013.01); *G01N 33/2045* (2019.01); *G01N 33/207* (2019.01);
(Continued)

(58) Field of Classification Search
CPC .... G01N 3/02; G01N 33/2045; G01N 33/207; G01N 2203/0067; G01N 2203/04;
(Continued)

(56) References Cited

U.S. PATENT DOCUMENTS 6,186,011 B1    2/2001 Wung et al.
10,746,641 B2 *  8/2020 Gupta ...................... G01N 3/20
(Continued)

FOREIGN PATENT DOCUMENTS

CN    208283180 U    12/2018
CN    109238610 A    1/2019
(Continued)

OTHER PUBLICATIONS

Extended European Search Report dated Nov. 6, 2023, issued in corresponding European Patent Application No. 21858448.0.
(Continued)

*Primary Examiner* — Freddie Kirkland, III
(74) *Attorney, Agent, or Firm* — Morgan, Lewis & Bockius LIP (57) ABSTRACT

The present technology relates to a method of inspecting a welding defect. The method includes: manufacturing an electrode assembly sample by welding an electrode lead on an electrode tab formed on an electrode assembly; measuring a tensile strength, a torsional strength and a peeling strength of a welded portion between the electrode tab and the electrode lead for the electrode assembly sample; deriving correlation between whether there is a welding defect and each of the tensile strength, the torsional strength, and the peeling strength; and deriving a reference value for
(Continued)

determining whether there is a welding defect for the tensile strength, the torsional strength, and the peeling strength, respectively.

15 Claims, 5 Drawing Sheets

(51) Int. Cl.
  *G01N 33/207* (2019.01)
  *H01M 10/48* (2006.01)
  *H01M 50/536* (2021.01)
(52) U.S. Cl.
  CPC ......... *H01M 10/48* (2013.01); *H01M 50/536* (2021.01); *G01N 2203/0067* (2013.01); *G01N 2203/04* (2013.01)
(58) Field of Classification Search
  CPC .. G01N 3/00; G01N 19/04; G01N 2203/0017; G01N 2203/0021; G01N 2203/0091; G01N 2203/0296; G01N 3/08; G01N 3/22; G01N 3/40; H01M 10/48; H01M 50/536; B23K 31/12; B23K 31/125; Y02E 60/10; Y02P 70/50
  See application file for complete search history.

(56) References Cited

U.S. PATENT DOCUMENTS

| | | |
|---|---|---|
| 2012/0193330 A1 | 8/2012 | Edwards, II et al. |
| 2015/0072201 A1 | 3/2015 | Kubota et al. |
| 2018/0275032 A1 | 9/2018 | Gupta |
| 2019/0152001 A1 | 5/2019 | Cai et al. |
| 2020/0044280 A1 | 2/2020 | Modeki et al. |
| 2020/0185690 A1 | 6/2020 | Kim et al. |

FOREIGN PATENT DOCUMENTS

| | | |
|---|---|---|
| JP | 2004-347527 A | 12/2004 |
| JP | 2013-84448 A | 5/2013 |
| JP | WO2012/066637 A1 | 5/2014 |
| JP | 6186658 B2 | 8/2017 |
| JP | 2018-111120 A | 7/2018 |
| JP | 2019-060769 A | 4/2019 |
| JP | 2020-513148 A | 4/2020 |
| KR | 2002-0008774 A1 | 1/2002 |
| KR | 10-0757623 B1 | 9/2007 |
| KR | 10-2012-0121414 A | 11/2012 |
| KR | 10-2014-0112466 A | 9/2014 |
| KR | 10-1452878 B1 | 10/2014 |
| KR | 10-2015-0049985 A | 5/2015 |
| KR | 10-2016-0057373 A | 5/2016 |
| KR | 10-2018-0101034 A | 9/2018 |
| KR | 10-2018-0122115 A | 11/2018 |

OTHER PUBLICATIONS

International Search Report (with translation) and Written Opinion dated Sep. 29, 2021 issued in corresponding International Patent Application No. PCT/KR2021/007545.
Office action issued Oct. 2, 2023, by the Japanese Patent Office corresponding to JP Application No. 2022-552350.
Office Action dated Sep. 26, 2024 issued in European Patent Application No. 21858448.0.
"Manual Arc Welding Technology," 1st edition, Guohua Du, pp. 273-274, China Machine Press, Published on Mar. 31, 1993.
Research and Practice on Modern Urban Municipal Facilities Construction, 1st edition, Guanyun Shi, pp. 386, China Science and Technology Press, Published on Jan. 31, 2008.
Office Action issued in related Chinese Patent Application No. 202180019270.5 dated Feb. 28, 2025.

\* cited by examiner

WELDING DEFECT INSPECTION METHOD

TECHNICAL FIELD

This application claims the benefit of priority based on Korean Patent Application No. 10-2020-0105340, filed on Aug. 21, 2020, and the entire contents of the Korean patent application are incorporated herein by reference.

The present invention relates to a method of inspecting a welding defect and a method of manufacturing a secondary battery including the method.

BACKGROUND ART

Recently, secondary batteries capable of charging and discharging have been widely used as energy sources of wireless mobile devices. In addition, the secondary battery has attracted attention as an energy source of an electric vehicle, a hybrid electric vehicle, etc., which are proposed as a solution for air pollution of existing gasoline vehicles and diesel vehicles using fossil fuel. Therefore, the types of applications using the secondary battery are currently much diversified due to the advantages of the secondary battery, and it is expected that the secondary battery will be applied to many fields and products in the future.

Such secondary batteries may be classified into lithium ion batteries, lithium ion polymer batteries, lithium polymer batteries, etc., depending on the composition of the electrode and the electrolyte, and among them, the amount of use of lithium-ion polymer batteries that are less likely to leak electrolyte and are easy to manufacture is on the increase. In general, secondary batteries are classified into cylindrical batteries and prismatic batteries in which an electrode assembly is embedded in a cylindrical or rectangular metal can, depending on the shape of a battery case, and pouch-type batteries in which the electrode assembly is embedded in a pouch-type case of an aluminum laminate sheet. The electrode assembly built into the battery case is composed of a positive electrode, a negative electrode, and a separator interposed between the positive electrode and the negative electrode, and is a power generating element capable of charging and discharging. The electrode assembly is classified into a jelly-roll type wound with a separator interposed between the positive electrode and the negative electrode which are long sheet-shaped and are coated with active materials, and a stack type in which a plurality of positive electrodes and negative electrodes of a predetermined size are sequentially stacked while a separator is interposed therebetween.

The positive electrode and the negative electrode are formed by applying a positive electrode slurry containing a positive electrode active material and a negative electrode slurry containing a negative electrode active material to a positive electrode current collector and a negative electrode current collector, followed by drying and rolling them. At this time, a little amount of binder is added to the positive electrode slurry and the negative electrode slurry to prevent the active material from being deintercalated from the current collector.

Further, a positive electrode tab and a negative electrode tab are formed at the positive electrode and the negative electrode for electric connection, and a positive electrode lead and a negative electrode lead are formed at the positive electrode tab and the negative electrode tab, respectively. At this time, the positive electrode tab and the positive electrode lead may be joined by welding, and the negative electrode tab and the negative electrode lead may also be joined by welding. At this time, since a welding defect may occur between the tab and the lead, welding defect inspection is performed to detect the welding defect.

When the welding defect inspection is performed, a welding strength of a welded portion between a tab and lead is generally measured. To this end, the tensile strength of the welded portion between the tab and the lead is mainly measured. Specifically, the tensile strength, which is generated as the tab and the lead are tensed in an opposite direction, is measured.

However, it is difficult to detect welding defects of all cases and intermittently generated small welding defects using only the tensile strength.

Hence, it is necessary to develop a method of inspecting a welding defect capable of detecting all small welding defects.

DISCLOSURE

Technical Problem

The present invention has been made to solve the above problems, and an object of the present invention is to provide a method of inspecting a welding defect having improved welding reliability and accuracy by detecting all small welding defects.

Technical Solution

A method of inspecting a welding defect according to an embodiment of the present invention includes: manufacturing an electrode assembly sample by welding an electrode lead on an electrode tab formed on an electrode assembly; measuring a tensile strength, a torsional strength and a peeling strength of a welded portion between the electrode tab and the electrode lead for the electrode assembly sample; deriving correlation between whether there is a welding defect and each of the tensile strength, the torsional strength, and the peeling strength; and deriving a reference value for determining whether there is a welding defect for the tensile strength, the torsional strength, and the peeling strength, respectively.

In a specific example, the measuring of the tensile strength, the torsional strength and the peeling strength includes: preparing three sets of electrode assembly samples; and measuring any one of the tensile strength, the torsional strength and the peeling strength per set.

The tensile strength, the torsional strength and the peeling strength are measured using a measuring apparatus including: a first gripper configured to fix an end of the electrode lead; and a second gripper configured to fix the electrode assembly.

At this time, the first gripper applies force to the electrode lead in a predetermined direction to thereby break the welded portion.

Further, in an embodiment of the present invention, the deriving of the correlation includes making a database about the correlation between the tensile strength, the torsional strength and the peeling strength of the welded portion between the electrode tab and the electrode lead and whether there is a welding defect.

At this time, the reference value is derived from the database.

In another embodiment of the present invention, the method of inspecting a welding defect further includes measuring the tensile strength, the torsional strength and the peeling strength of the welded portion between the electrode tab and the electrode lead by using different welding methods, and deriving correlation between whether there is a welding defect and each of the tensile strength, the torsional strength, and the peeling strength for each of the welding methods.

At this time, the method of inspecting a welding defect according to the present invention further includes deriving a reference value for determining whether there is a welding defect for each of the welding methods.

The welding methods include a ultrasonic welding or a laser welding.

The method of inspecting a welding defect according to the present invention further includes determining a cause of generation of a welding defect from the correlation and making a database based thereon.

Further, the method of inspecting a welding defect according to the present invention further includes determining a welding defect of the electrode assembly.

At this time, the determining of the welding defect includes: preparing three sets of electrode assemblies to be inspected by welding electrode leads on electrode tabs; measuring any one of a tensile strength, a torsional strength, and a peeling strength for each set; and determining whether there is a welding defect by comparing a measured value obtained by the measuring with a reference value.

At this time, the determining of whether is a welding defect includes comparing the measured value with the reference value for two of the tensile strength, the torsional strength and the peeling strength.

Further, the determining of whether is a welding defect includes comparing the measured value with the reference value for the tensile strength, the torsional strength and the peeling strength.

Further, the present invention provides a method of manufacturing a secondary battery including the method of inspecting a welding defect as described above.

Advantageous Effects

According to the welding defect inspection method of the present invention, the inspection method can be applied all welding processes by checking the correlation between whether there is a welding defect and each of the tensile strength, the torsional strength, and the peeling strength and standardizing the correlation.

Further, with respect to the welding strength, by measuring other strength values in addition to the tensile strength and deriving the reference value therefrom, it is possible to detect small welding defects, and the reliability and accuracy of the welding may be improved.

DETAILED DESCRIPTION OF THE PREFERRED EMBODIMENTS

Hereinafter, the present invention will be described in detail with reference to the drawings. The terms and words used in the present specification and claims should not be construed as limited to ordinary or dictionary terms and the inventor may properly define the concept of the terms in order to best describe its invention. The terms and words should be construed as meaning and concept consistent with the technical idea of the present invention.

In this application, it should be understood that terms such as "include" or "have" are intended to indicate that there is a feature, number, step, operation, component, part, or a combination thereof described on the specification, and they do not exclude in advance the possibility of the presence or addition of one or more other features or numbers, steps, operations, components, parts or combinations thereof. Also, when a portion such as a layer, a film, an area, a plate, etc. is referred to as being "on" another portion, this includes not only the case where the portion is "directly on" the another portion but also the case where further another portion is interposed therebetween. On the other hand, when a portion such as a layer, a film, an area, a plate, etc. is referred to as being "under" another portion, this includes not only the case where the portion is "directly under" the another portion but also the case where further another portion is interposed therebetween. In addition, to be disposed "on" in the present application may include the case disposed at the bottom as well as the top.

Hereinafter, the present invention will be described in detail with reference to the drawings.

Figure 1:
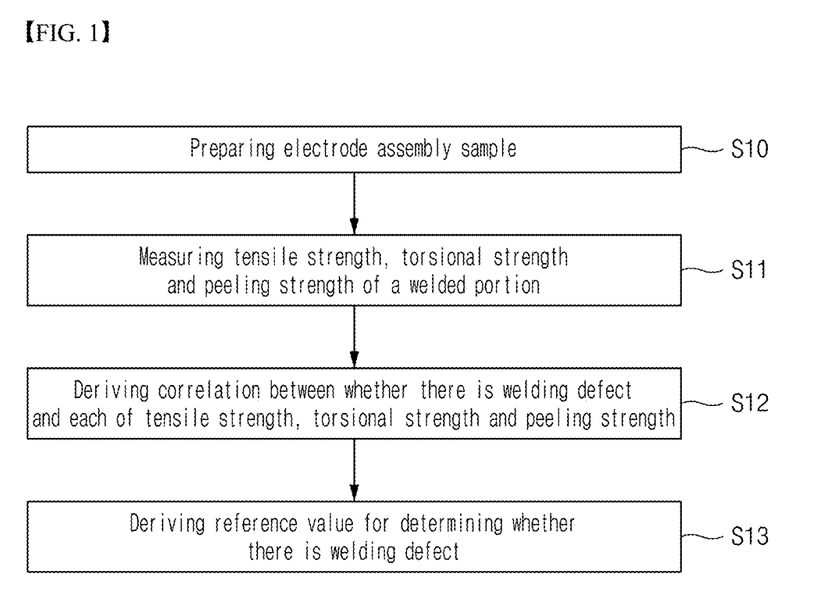
FIG. 1 is a flowchart illustrating the order of a method of inspecting a welding defect according to an embodiment of the present invention.

FIG. 1 is a flowchart illustrating the order of a method of inspecting a welding defect according to an embodiment of the present invention.

Referring to FIG. 1, a method of inspecting a welding defect according to an embodiment of the present invention includes: manufacturing an electrode assembly sample by welding an electrode lead on an electrode tab formed on an electrode assembly (s10); measuring a tensile strength, a torsional strength and a peeling strength of a welded portion between the electrode tab and the electrode lead for the electrode assembly sample (s20); deriving correlation between whether there is a welding defect and each of the tensile strength, the torsional strength, and the peeling strength (s30); and deriving a reference value for determining whether there is a welding defect for the tensile strength, the torsional strength, and the peeling strength, respectively (s40).

As described above, the tensile strength of the welded portion between the tab and the lead was measured for a general welding defect inspection. However, since the welding strength for only one direction can be recognized by such a tensile strength inspection, it is difficult to detect welding defects of all cases and intermittently generated small welding defects.

According to the welding defect inspection method of the present invention, the inspection method can be applied all welding processes by checking the correlation between the tensile strength, the torsional strength and the peeling strength as the welding strength and whether there is a welding defect and standardizing the correlation.

Further, with respect to the welding strength, by measuring other strength values in addition to the tensile strength and deriving the reference value therefrom, it is possible to detect small welding defects, and the reliability and accuracy of the welding may be improved.

Hereinafter, each step of the welded defect inspection method according to the present invention will be described in detail.

In the specification of the present invention, the welding strength includes a tensile strength, a torsional strength, and a peeling strength as the strength at a welded portion between an electrode tab and an electrode lead.

<Preparation of Electrode Assembly Sample>

In the welding defect inspection method according to the present invention, an electrode assembly sample is manufactured by welding an electrode lead on an electrode tab formed on an electrode assembly.

At this time, the electrode assembly has a structure in which a positive electrode, a separator and a negative electrode are alternately stacked, and the positive electrode and the negative electrode may respectively have a structure in which an active material layer is formed through the drying and rolling process after an electrode slurry containing an electrode active material is applied on a current collector.

The current collector may be a positive electrode current collector or a negative electrode current collector, and the electrode active material may be a positive electrode active material or a negative electrode active material. In addition, the electrode slurry may further include a conductive material and a binder in addition to the electrode active material.

In the present invention, the positive electrode collector generally has a thickness of 3 to 500 micrometers. The positive electrode current collector is not particularly limited as long as it has high conductivity without causing a chemical change in the battery. Examples of the positive electrode current collector include stainless steel, aluminum, nickel, titanium, sintered carbon or aluminum or stainless steel of which the surface has been treated with carbon, nickel, titanium, silver, or the like. The current collector may have fine irregularities on the surface thereof to increase the adhesion of the positive electrode active material, and various forms such as a film, a sheet, a foil, a net, a porous body, a foam, and a nonwoven fabric are possible.

The sheet for the negative electrode collector generally has a thickness of 3 to 500 micrometers. The negative electrode current collector is not particularly limited as long as it has electrical conductivity without causing chemical changes in the battery, and examples thereof include copper, stainless steel, aluminum, nickel, titanium, sintered carbon, copper or stainless steel of which the surface has been treated with carbon, nickel, titanium, silver or the like, aluminum-cadmium alloy, or the like. In addition, like the positive electrode current collector, fine unevenness can be formed on the surface to enhance the bonding force of the negative electrode active material, and it can be used in various forms such as a film, a sheet, a foil, a net, a porous body, a foam, and a nonwoven fabric.

In the present invention, the positive electrode active material is a material capable of causing an electrochemical reaction and a lithium transition metal oxide, and contains two or more transition metals. Examples thereof include: layered compounds such as lithium cobalt oxide ($LiCoO_2$) and lithium nickel oxide ($LiNiO_2$) substituted with one or more transition metals; lithium manganese oxide substituted with one or more transition metals; lithium nickel oxide represented by the formula $LiNi_{1-y}M_yO_2$ (wherein M=Co, Mn, Al, Cu, Fe, Mg, B, Cr, Zn or Ga and contains at least one of the above elements, $0.01 \leq y \leq 0.7$); lithium nickel cobalt manganese composite oxide represented by the formula $Li_{1+z}Ni_bMn_cCo_{1-(b+c+d)}M_dO_{(2-c)}A_c$ such as $Li_{1+z}Ni_{1/3}Mn_{1/3}O_2$, $Li_{1+z}Ni_{0.4}Mn_{0.4}Co_{0.2}O_2$ etc. (wherein $-0.5 \leq z \leq 0.5$, $0.1 \leq b \leq 0.8$, $0.1 \leq c \leq 0.8$, $0 < d \leq 0.2$, $0 \leq e \leq 0.2$, $b+c+d<1$, M=Al, Mg, Cr, Ti, Si or Y, and A=F, P or Cl); olivine-based lithium metal phosphate represented by the formula $Li_{1+x}M_{1-y}M'_yPO_{4-z}X_z$ (wherein M=transition metal, preferably Fe, Mn, Co or Ni, M'=Al, Mg or Ti, X=F, S or N, and $-0.5 \leq x \leq 0.5$, $0 \leq y \leq 0.5$, $0 \leq z \leq 0.1$).

Examples of the negative electrode active material include carbon such as non-graphitized carbon and graphite carbon; metal complex oxide such as $Li_xFe_2O_3 (0 \leq x \leq 1)$, $Li_xWO_2 (0 \leq x \leq 1)$, $Sn_xMe_{1-x}Me'_yO_z$ (Me: Mn, Fe, Pb, Ge; Me': Al, B, P, Si, groups 1, 2, and 3 of the periodic table, halogen; $0 \leq x \leq 1$; $1 \leq y \leq 3$; $1 \leq z \leq 8$); lithium alloy; silicon alloy; tin alloy; metal oxides such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, and $Bi_2O_5$; conductive polymers such as polyacetylene; and Li—Co—Ni-based materials.

The conductive material is usually added in an amount of 1 to 30% by weight based on the total weight of the mixture including the positive electrode active material. Such a conductive material is not particularly limited as long as it has electrical conductivity without causing a chemical change in the battery, and examples thereof include graphite such as natural graphite and artificial graphite; carbon black such as carbon black, acetylene black, Ketjen black, channel black, furnace black, lamp black, and summer black; conductive fibers such as carbon fiber and metal fiber; metal powders such as carbon fluoride, aluminum and nickel powder; conductive whiskey such as zinc oxide and potassium titanate; conductive metal oxides such as titanium oxide; and conductive materials such as polyphenylene derivatives and the like.

The binder is added in an amount of 1 to 30% by weight, on the basis of the total weight of the mixture containing the positive electrode active material, as a component that assists in bonding between the active material and the conductive material and bonding to the current collector. Examples of such binders include polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, ethylene-propylene-diene terpolymer (EPDM), sulfonated EPDM, styrene butylene rubber, fluorine rubber, various copolymers and the like.

Further, the separator is interposed between the positive electrode and the negative electrode, and an insulating thin film having high ion permeability and mechanical strength is used. The pore diameter of the separator is generally 0.01 to 10 micrometers, and the thickness is generally 5 to 300 micrometers. Examples of such a separator include olefin-based polymers such as polypropylene which is chemically resistant and hydrophobic; a sheet or a nonwoven fabric made of glass fiber, polyethylene or the like.

In an electrode assembly, an electrode tab is formed at one side of an electrode, and the electrode tab may be a positive electrode tab or a negative electrode tab. A positive electrode lead and a negative electrode lead are connected to the positive electrode tab and the negative electrode tab, respectively. The positive electrode lead and the negative electrode lead are drawn to the outside to thereby play a role of a terminal which is electrically connected to the outside. At this time, the positive electrode lead and the negative electrode lead may be joined to the positive electrode tab and the negative electrode tab, respectively, by welding. Known welding methods may be used. For example, a ultrasonic welding or a laser welding may be used.

<Measurement of Welding Strength>

When an electrode assembly sample is manufactured, the welding strength, that is, the tensile strength, the torsional strength and the peeling strength, of the welded portion is measured for the electrode assembly sample. In the welding defect inspection method according to the present invention, two or more kinds of welding strength may be measured according to the direction of the external force.

Namely, according to the welding defect inspection method of the present invention, it is possible to detect all small welding defects by adding the torsional strength and the peeling strength, which are measured as external force in a direction that is different from that of the tensile strength is applied, in addition to the tensile strength, as the evaluation standard for determining the welding defect, thereby improving reliability and accuracy of welding.

The measuring of the tensile strength, the torsional strength and the peeling strength includes: preparing three sets of electrode assembly samples; and measuring any one of the tensile strength, the torsional strength and the peeling strength per set.

As will be described later, the tensile strength, the torsional strength and the peeling strength are measured by breaking a welded portion between an electrode tab and an electrode lead by applying external force to the electrode tab in a constant direction. As such, it is not possible to measure a different kind of welding strength with the electrode assembly sample which has already been measured for one kind of welding strength. Hence, three sets are prepared, and one of the tensile strength, the torsional strength and the peeling strength is measured for each set. Herein, one set includes at least one electrode assembly sample, and one set may include two or more electrode assembly samples. At this time, if one set includes two or more electrode assembly samples, the average of welding strengths of two electrode assembly samples may be determined as the welding strength of the set.

Further, the tensile strength, the torsional strength and the peeling strength may be measured using the same form of measuring apparatus.

Figure 2:
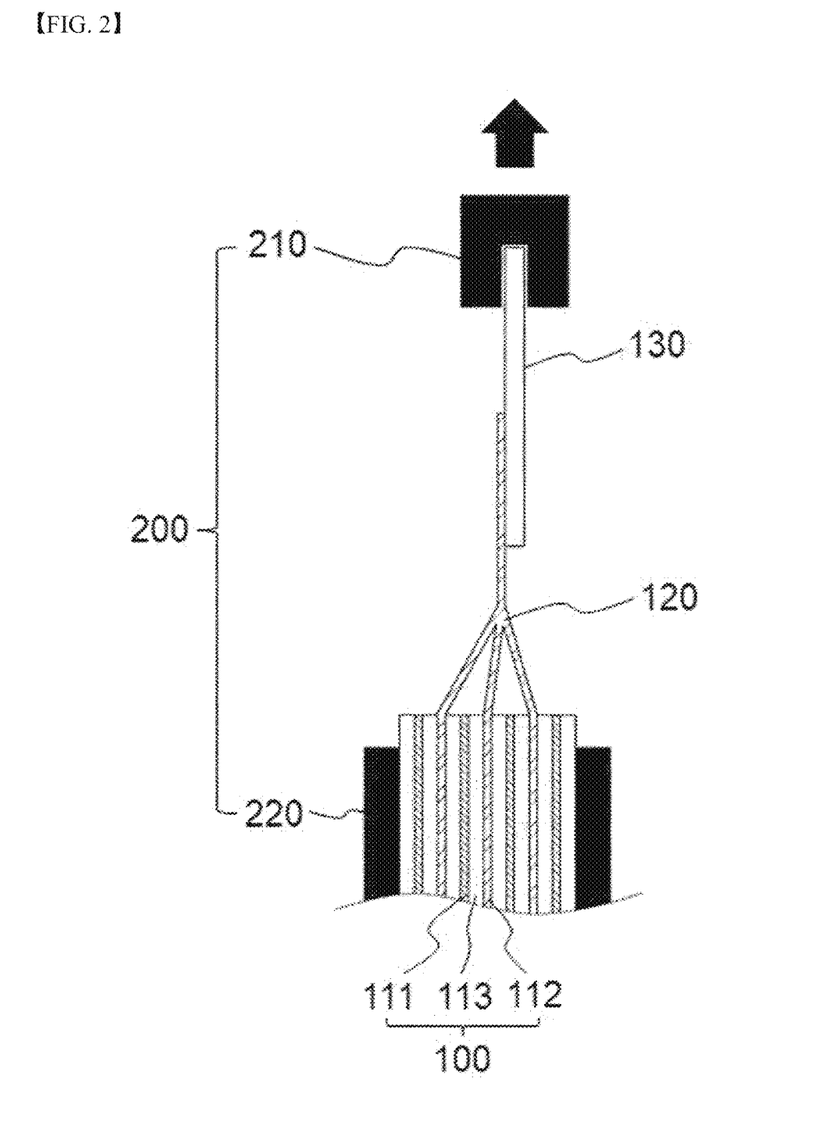
FIG. 2 is a schematic diagram illustrating a method of measuring a tensile strength in a method of inspecting a welding defect according to the present invention.
Figure 3:
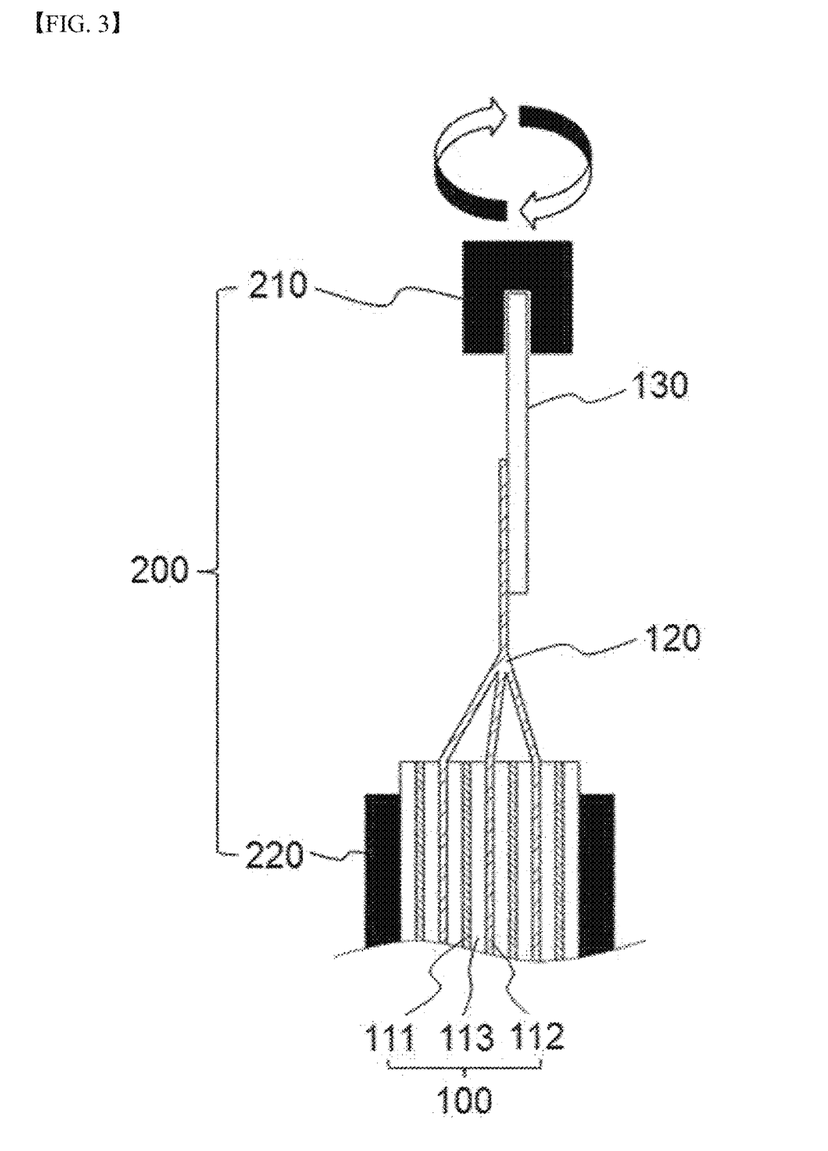
FIG. 3 is a schematic diagram illustrating a method of measuring a torsional strength in a method of inspecting a welding defect according to the present invention.
Figure 4:
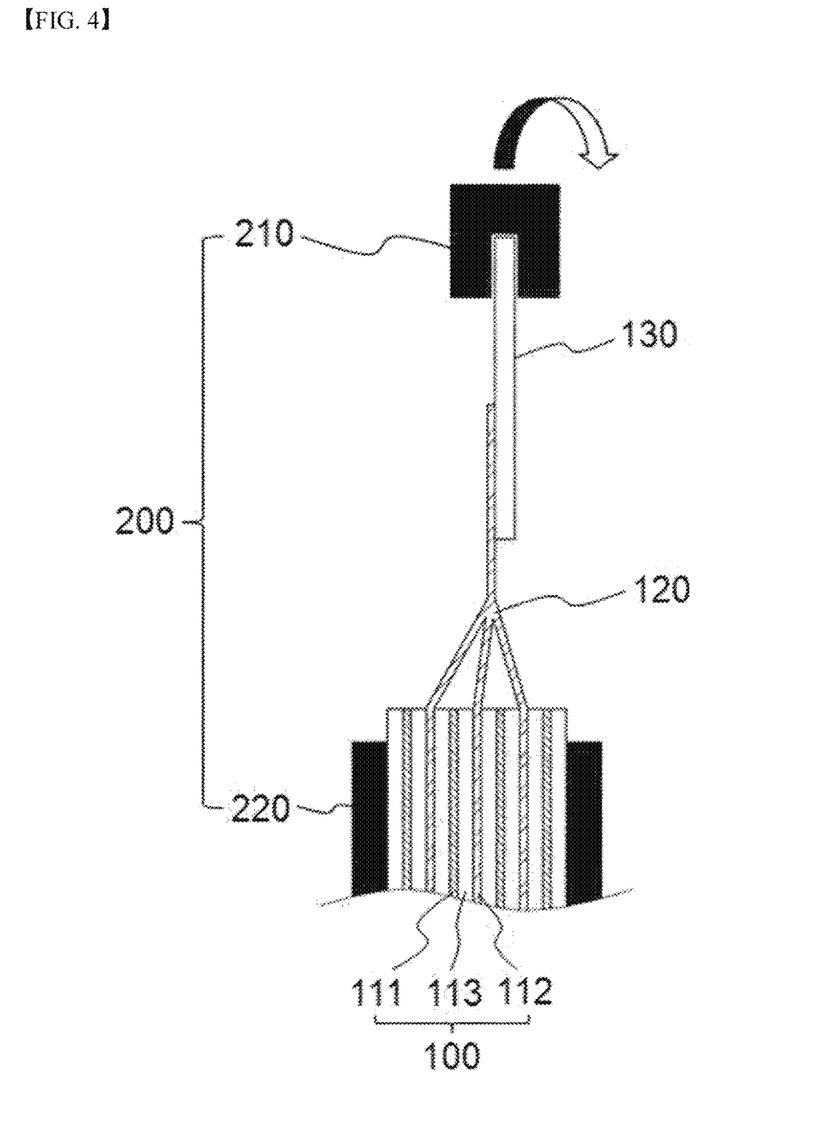
FIG. 4 is a schematic diagram illustrating a method of measuring a peeling strength in a method of inspecting a welding defect according to the present invention.

FIG. 2 is a schematic diagram illustrating a method of measuring a tensile strength in a method of inspecting a welding defect according to the present invention, and FIG. 3 is a schematic diagram illustrating a method of measuring a torsional strength in a method of inspecting a welding defect according to the present invention. FIG. 4 is a schematic diagram illustrating a method of measuring a peeling strength in a method of inspecting a welding defect according to the present invention.

Referring to FIGS. 2 to 4, an electrode assembly 100 has a structure in which a positive electrode 111, a negative electrode 112 and a separator 113 are alternately stacked. Herein, an electrode tab 120, which is one of a positive electrode tab and a negative electrode tab, is formed at one side of the electrode assembly 100, and an electrode lead 130 is joined to the electrode tab by welding.

Further, the measuring apparatus 200 includes a first gripper 210 configured to fix the end of the electrode lead; and a second gripper 220 configured to fix the electrode assembly.

Specifically, the second gripper 220 fixes the electrode assembly 100. The second gripper 220 may have a structure that one pair of pressing plates are formed on surfaces contacting the electrode assembly 100 to press the electrode assembly 110 from two surfaces. The one pair of pressing plates may be fixed by appropriately pressing the electrode assembly through interval adjustment.

The first gripper 210 may have a structure in which a space for accommodating the electrode lead 130 is formed to fix the end of the electrode lead 130, for example, a structure in which one pair of pressing plates are formed on the surface contacting the electrode lead. In this case, the pressing plate may appropriately adjust the interval to thereby fix the electrode lead. In the present invention, the first gripper 210 and the second gripper 220 may fix the electrode assembly and the electrode lead and there is no specific limitation on their form.

At this time, the first gripper 210 applies force to the electrode lead in a predetermined direction to thereby break the welded portion.

Referring to FIG. 2, the first gripper 210 may apply tensile force to the welded portion between the electrode lead 130 and the electrode tab 120 by pulling the electrode lead 130 to be parallel to the drawn direction. The first gripper 210 may pull the electrode lead 130 until the welded portion is broken, and the force, which is applied to the welded portion at the time of breakage, may be defined as the tensile strength of the welded portion. The force, which is applied to the welded portion at the time of breakage, may be measured using a known measuring device, etc.

Referring to FIG. 3, the first gripper 210 may apply torsional force to the welded portion between the electrode lead 130 and the electrode tab 120 by rotating by using the central portion in the width direction of the electrode lead as the rotation shaft. The first gripper 210 rotate until the welded portion is broken, and the force, which is applied to the welded portion at the time of breakage, may be defined as the torsional strength of the welded portion. Likewise, the force, which is applied to the welded portion at the time of breakage, may be measured using a known measuring device, etc.

Referring to FIG. 4, the first gripper 210 may apply force to peel off the electrode lead 130 from the electrode tab 120 while applying force in a direction perpendicular to a direction in which the electrode tab 120 or the electrode lead 130 are drawn. The first gripper 210 may apply force until the welded portion is broken, and the force, which is applied to the welded portion at the time of breakage, may be defined as the peeling strength of the welded portion. Likewise, the force, which is applied to the welded portion at the time of breakage, may be measured using a known measuring device, etc.

The welding strength may be measured for each of a plurality of electrode assembly samples, and as will be described later, the welding strength may be measured for electrode assembly samples by different welding methods.

<Deriving Correlation with Whether there is a Welding Defect>

When the a tensile strength, a torsional strength and a peeling strength are measured for an electrode assembly sample, the correlation between whether there is a welding defect and each of the tensile strength, the torsional strength, and the peeling strength is derived. Herein, the correlation refers to a tendency indicated by whether there is a welding defect according to the numerical value of the tensile strength, the torsional strength and the peeling strength.

Specifically, the deriving of the correlation includes making a database about the correlation between the tensile strength, the torsional strength and the peeling strength of the welded portion between the electrode tab and the electrode lead and whether there is a welding defect. This is to recognize the tendency of whether there is a welding defect for the tensile strength, the torsional strength and the peeling strength. To this end, the tensile strength, the torsional strength and the peeling strength are respectively measured after manufacturing a plurality of electrode assembly samples, and the measured information may be saved in a storage system such as a memory. Further, such a database may be recorded in visual data such as tables or graphs. At this time, it is preferable to measure the tensile strength, the torsional strength and the peeling strength for a large number of electrode assembly samples for the accuracy of the measurement.

Herein, whether there is a welding defect indicates whether there has actually been a defect at a welded portion between an electrode lead and an electrode tab. For example, it may be determined by observing the external appearance of the welded portion or the surface state of the welded portion.

<Deriving a Reference Value>

After deriving the correlation between whether there is a welding defect and each of the tensile strength, the torsional strength, and the peeling strength, reference values for determining whether there is a welding defect are derived therefrom. The reference value is derived from the database. Herein, the reference value is derived for each of the tensile strength, the torsional strength and the peeling strength.

Specifically, the measurement value information for the tensile strength, the torsional strength and the peeling strength of electrode assembly samples determined as having a welding defect, and the measurement value information for the tensile strength, the torsional strength and the peeling strength of electrode assembly samples determined as having no welding defect, are saved in the database. Herein, for example, the minimum value among the measurement values for the tensile strength, the torsional strength and the peeling strength of the electrode assembly samples determined as having no welding defect may be determined as the reference value.

Namely, according to the welding defect inspection method of the present invention, the inspection method can be applied all welding processes by checking the correlation between whether there is a welding defect and each of the tensile strength, the torsional strength, and the peeling strength and standardizing the correlation.

Further, with respect to the welding strength, by measuring other strength values in addition to the tensile strength and deriving the reference value therefrom, it is possible to detect small welding defects, and the reliability and accuracy of the welding may be improved.

Further, in another embodiment of the present invention, the method of inspecting a welding defect includes measuring the tensile strength, the torsional strength and the peeling strength of the welded portion between the electrode tab and the electrode lead by using different welding methods, and deriving correlation between whether there is a welding defect and each of the tensile strength, the torsional strength, and the peeling strength for each of the welding methods. Further, the welding defect inspection method further includes deriving a reference value for determining whether there is a welding defect for each of the welding methods.

Figure 5:
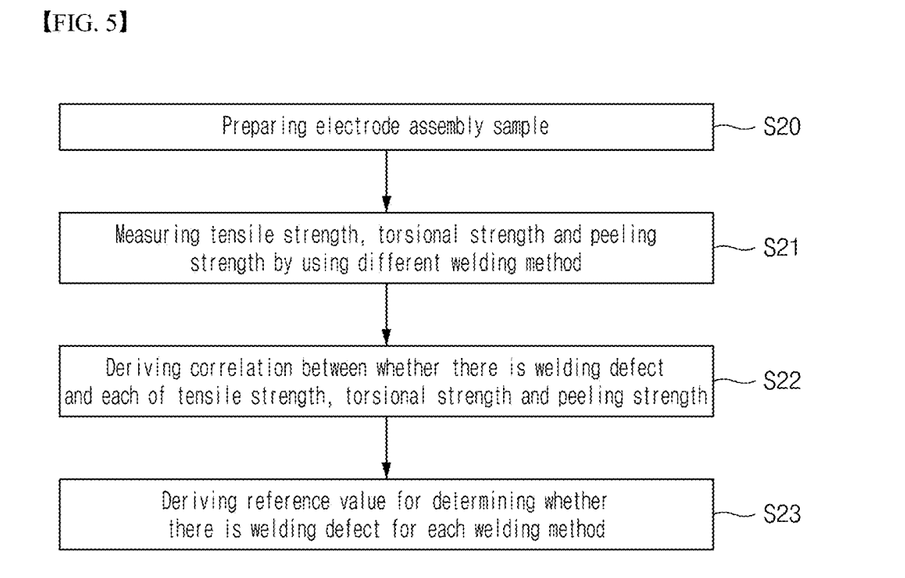
FIG. 5 is a flowchart illustrating the order of a method of inspecting a welding defect according to another embodiment of the present invention.

FIG. 5 is a flowchart illustrating the order of a method of inspecting a welding defect according to another embodiment of the present invention.

Namely, referring to FIG. 5, a method of inspecting a welding defect includes: manufacturing an electrode assembly sample by welding an electrode lead on an electrode tab formed on an electrode assembly (s20); measuring a tensile strength, a torsional strength and a peeling strength of a welded portion between the electrode tab and the electrode lead for the electrode assembly sample by using different welding methods (s21); deriving correlation between whether there is a welding defect and each of the tensile strength, the torsional strength, and the peeling strength (s22); and deriving a reference value for determining whether there is a welding defect for each of the welding methods (s23).

Herein, the welding methods may include laser welding and ultrasonic welding.

Namely, the present invention may reflect deviation of the welding strength which may vary according to the welding method by differentiating the reference value according to the welding method in the process of deriving the reference value for determining whether there is a welding defect.

Herein, each step in the welding defect inspection method is the same as described above. Specifically, three sets of electrode assembly samples are prepared using one welding method, and then one of the tensile strength, the torsional strength and the peeling strength is measured for each set. Further, the same process is repeated using different welding methods.

At this time, the measuring apparatus may include a first gripper configured to fix the end of the electrode lead, and a second gripper configured to fix the electrode assembly.

Meanwhile, when the welding strength is measured, the correlation between whether there is a welding defect and each of the tensile strength, the torsional strength, and the peeling strength for each welding method is derived from the measured welding strength. At this time, a step of determining the cause of generation of a welding defect from the tensile strength, the torsional strength and the peeling strength according to the welding method and making a database based thereon. To this end, the tensile strength, the torsional strength and the peeling strength are respectively measured after manufacturing a plurality of electrode assembly samples using different welding methods, and the measured information may be saved in a storage system such as a memory. Further, such a database may be recorded in visual data such as tables or graphs. Further, the reference value may be derived from such a database. The specific process for deriving the reference value may be the same as described above.

Further, the method of inspecting a welding defect according to the present invention further includes determining a cause of generation of a welding defect from the correlation and making a database based thereon. When different welding methods are used, causes of welding defects are also different. Hence, in the present invention, the tensile strength, the torsional strength and the peeling strength according to the welding method and the cause of the welding defect may be made as a database, and the database may be utilized as reference data for finding out the cause of the welding defect when such a welding defect occurs.

Likewise, when the reference value for whether there is a welding defect is secured, the step of determining whether there is a welding defect in the electrode assembly is performed based thereon.

The step of determining whether there is a welding defect includes preparing three sets of electrode assemblies to be inspected by welding an electrode lead on an electrode tab, measuring one of the tensile strength, the torsional strength and the peeling strength for each set, and comparing the measurement value with the reference value to determine whether there is a welding defect.

Specifically, the method of manufacturing the electrode assembly and the method of measuring the tensile strength, the torsional strength and the peeling strength are the same as described above. The tensile strength, the torsional strength and the peeling strength may be measured by a measuring apparatus described above, and a different welding strength may be measured per set.

When the tensile strength, the torsional strength and the peeling strength are measured, they are compared with the reference value to determine whether there is a welding defect. At this time, the determining of whether is a welding defect includes comparing the measured value with the reference value for two of the tensile strength, the torsional strength and the peeling strength. In this case, for example, the measurement value is compared with the reference value for any two of the tensile strength, the torsional strength and the peeling strength, and if the measurement value satisfies the reference value requirement for the two, the electrode assembly may be determined as a good product. In this case, the electrode assembly determined as a good product may be an electrode assembly manufactured in the same process line.

Further, in another example, the determining of whether is a welding defect includes comparing the measured value with the reference value for the tensile strength, the torsional strength and the peeling strength. In this case, for example, the measurement value is compared with the reference value for all of the tensile strength, the torsional strength and the peeling strength, and if the measurement value satisfies the reference value requirement for all of the tensile strength, the torsional strength and the peeling strength, the electrode assembly may be determined as a good product. As described above, the electrode assembly determined as a good product may be an electrode assembly manufactured in the same process line.

Further, the present invention provides a method of manufacturing a secondary battery including the method of inspecting a welding defect as described above.

Specifically, the secondary battery is manufactured as an electrode assembly having a structure, in which a positive electrode, a separator and a negative electrode are alternately stacked, is accommodated in a battery case. At this time, the same as the above-described electrode assembly sample may be used as the positive electrode, the negative electrode and the separator. Further, what was determined as a good product when performing inspection according to the welding defect inspection method as described above may be used as the electrode assembly.

Further, the battery case is not particularly limited as long as it is used as an exterior material for packaging the battery, and a cylindrical, square, or pouch type may be used and specifically a pouch-type battery case may be used. Likewise, details about the battery case are known to those of ordinary skill in the art, and thus the detailed description thereof is omitted here.

When an electrode assembly is accommodated in a battery case, an electrolyte solution is injected and the battery case is sealed, and then a formation process is performed, to thereby manufacture a secondary battery.

The above description is merely illustrative of the technical idea of the present invention, and those skilled in the art to which the present invention pertains may make various modifications and variations without departing from the essential characteristics of the present invention. Therefore, the drawings disclosed in the present invention are not intended to limit the technical idea of the present invention but to describe the present invention, and the scope of the technical idea of the present invention is not limited by these drawings. The scope of protection of the present invention should be interpreted by the following claims, and all technical ideas within the scope equivalent thereto should be construed as being included in the scope of the present invention.

On the other hand, in this specification, terms indicating directions such as up, down, left, right, before, and after are used, but it is obvious that these terms are for convenience of description only and may change depending on the location of the object or the location of the observer.

DESCRIPTION OF REFERENCE NUMERALS

100: electrode assembly
111: positive electrode
112: negative electrode
113: separator
120: electrode tab
130: electrode lead
200: measuring apparatus
210: first gripper
220: second gripper

The invention claimed is:

1. A method of inspecting a welding defect, comprising:
manufacturing an electrode assembly sample by welding an electrode lead on an electrode tab formed on the electrode assembly sample;
measuring a tensile strength, a torsional strength and a peeling strength of a welded portion between the electrode tab and the electrode lead for the electrode assembly sample;
deriving correlation between whether there is a welding defect and each of the tensile strength, the torsional strength, and the peeling strength; and
deriving a reference value for determining whether there is a welding defect for the tensile strength, the torsional strength, and the peeling strength, respectively.

2. The method of claim 1, wherein the measuring of the tensile strength, the torsional strength and the peeling strength includes:
preparing three sets of the electrode assembly samples; and
measuring any one of the tensile strength, the torsional strength and the peeling strength per set.

3. The method of claim 1, wherein the tensile strength, the torsional strength and the peeling strength are measured using a measuring apparatus including:
a first gripper configured to fix an end of the electrode lead; and
a second gripper configured to fix the electrode assembly sample.

4. The method of claim 3, wherein the first gripper applies force to the electrode lead in a predetermined direction to thereby break the welded portion.

5. The method of claim 1, wherein the deriving of the correlation includes making a database about the correlation between the tensile strength, the torsional strength and the peeling strength of the welded portion between the electrode tab and the electrode lead and whether there is a welding defect.

6. The method of claim 5, wherein the reference value is derived from the database.

7. The method of claim 1, wherein the measuring the tensile strength, the torsional strength and the peeling strength comprises using different welding methods, and deriving correlation between whether there is a welding defect and each of the tensile strength, the torsional strength, and the peeling strength for each of the welding methods.

8. The method of claim 7, further comprising deriving a reference value for determining whether there is a welding defect for each of the welding methods.

9. The method of claim 8, wherein the welding methods include an ultrasonic welding or a laser welding.

10. The method of claim 7, further comprising determining a cause of generation of a welding defect from the correlation and making a database about the correlation.

11. The method of claim 1, further comprising determining a welding defect of the electrode assembly sample.

12. The method of claim 11, wherein the determining the welding defect comprises:
preparing three sets of electrode assemblies to be inspected by welding electrode leads on electrode tabs;
measuring any one of a tensile strength, a torsional strength, and a peeling strength for each set; and
determining whether there is a welding defect by comparing a measured value obtained by the measuring with a reference value.

13. The method of claim 12, wherein the determining of whether there is a welding defect includes comparing the measured value with the reference value for two of the tensile strength, the torsional strength and the peeling strength.

14. The method of claim 12, wherein the determining whether there is a welding defect includes comparing the measured value with the reference value for the tensile strength, the torsional strength and the peeling strength.

15. A method of manufacturing a secondary battery comprising the method of inspecting a welding defect according to claim 1.

* * * * *